(12) United States Patent
Kaufman

(10) Patent No.: US 6,839,455 B2
(45) Date of Patent: Jan. 4, 2005

(54) SYSTEM AND METHOD FOR PROVIDING INFORMATION FOR DETECTED PATHOLOGICAL FINDINGS

(76) Inventor: Scott Kaufman, 6860 SW. 194 Ave., Pembroke Pines, FL (US) 33332

( * ) Notice: Subject to any disclaimer, the term of this patent is extended or adjusted under 35 U.S.C. 154(b) by 95 days.

(21) Appl. No.: 10/273,502

(22) Filed: Oct. 18, 2002

(65) Prior Publication Data
US 2004/0075433 A1 Apr. 22, 2004

(51) Int. Cl.[7] ............................................. G06K 9/00
(52) U.S. Cl. ...................................... 382/128; 600/407
(58) Field of Search ............................... 382/128, 129, 382/130, 131, 132; 600/407, 437; 324/300, 306, 307, 309

(56) References Cited

U.S. PATENT DOCUMENTS

| | | | |
|---|---|---|---|
| 5,570,384 A | | 10/1996 | Nishida et al. |
| 5,938,607 A | * | 8/1999 | Jago et al. .................. 600/437 |
| 6,058,322 A | * | 5/2000 | Nishikawa et al. ......... 600/408 |
| 6,400,151 B1 | | 6/2002 | Haase et al. |
| 6,400,157 B1 | | 6/2002 | Bonanni et al. |
| 6,480,186 B1 | * | 11/2002 | McCabe et al. ............. 345/168 |

* cited by examiner

Primary Examiner—Louis Arana
(74) Attorney, Agent, or Firm—Kenneth Watov; Watov & Kipnes, P.C.

(57) ABSTRACT

A system and method of providing information concerning pathological findings evidenced by radiographical reports. A medical care provider may request a radiographical image, in particular, an MRI image of a region of the body. The region of the patient's body is scanned and the images are read and interpreted to determine if there is a positive finding of a pathology. If a pathology is detected, the generated scanned images are reviewed for a radiographical image that best depicts the detected pathology and the image is selected for further annotation. The image is then annotated to highlight and more fully describe and delineate the pathology thus alerting the medical care provider of the pathology's existence. In addition, the report may be further delineated with an identifying mark informing the referring physician of a positive finding of a pathology.

34 Claims, 8 Drawing Sheets

PATIENT'S DATABASE 260

| Patient Identifier 302 | HEADER INFORMATION 305 ||||||  Patient's Images 370 |
| --- | --- | --- | --- | --- | --- | --- | --- |
|  | Patient's Name 310 | Sex 320 | Birth Date 330 | Referring Physician 340 | Study Description 350 | Examination Date 360 |  |
| 111 | John Doe | M | 1/15/52 | Dr. Alpha | Right Foot | 1/5/02 | image#1 |
| 222 | Mary Purple | F | 2/2/72 | Dr. Roe | Lower Back | 2/4/02 | image#2 |
| 333 | Bob Smith | M | 3/3/63 | Dr. Gamma | Left Thigh | 3/5/02 | image#3 |
| 444 | Jane Doe | F | 4/4/84 | Dr. Pi | Left Knee | 6/7/02 | image#4 |

IMPRESSION: LEFT LATERAL DISC HERNIATION @ L4/5. RIGHT PARACENTRAL DISK HERNIATION @ L5/S1.

Fig. 6

SYSTEM AND METHOD FOR PROVIDING INFORMATION FOR DETECTED PATHOLOGICAL FINDINGS

FIELD OF THE INVENTION

This invention generally relates to a business method and more particularly, to a system and method of providing information concerning pathological findings evidenced by radiographical reports.

BACKGROUND OF INVENTION

Magnetic Resonance Imaging (MRI) is a well-known diagnostic tool that is primarily used by doctors to view internal images of the human body from various angles without the use of x-rays or invasive procedures. MRIs provide the added benefit of producing imaging results in a relatively short period of time. A MRI image also provides basic biomedical and anatomical information in such precise detail that it facilitates early diagnosis of injuries, diseases or abnormalities. When a patient is scanned, internal images of the body are produced by nuclear magnetic resonance. The images are represented in contrast by light and dark areas depending on the density and structure of the region of the body being scanned. The scanned image is then interpreted to distinguish between normal and abnormal states.

Generally, a radiologist reads and interprets the MRI image for pathological findings and prepares a report of the findings. The report and the accompanying images are submitted to the referring physician which may not be viewed until the patient returns for their next scheduled visit. Unfortunately, unless a doctor is extremely vigilant and careful, a detected pathology may remain unnoticed and/or untreated until the patient's next scheduled visit. This is because the physician may have limited resources available to review incoming reports in order to satisfy the demands of their medical practice at the time.

SUMMARY OF THE INVENTION

Thus, there remains a need for an improved way of handling the reporting of pathologies evidenced from a MRI report. The system and method described herein provides a solution for that problem.

According to one embodiment, the invention is a method of providing information concerning pathological findings that allows a physician to be readily alerted to the existence of a pathology, which may include but is not limited to a disease, an injury and/or abnormality. The method involves receiving patient's demographic information, for example, name, sex, birth date, as well as a study description detailing the region of the patient's body to be imaged. During a magnetic resonance imaging procedure the patient is placed into an imaging volume of a magnet which generates a static magnetic field. Generally the procedure comprises of a predetermined scanning sequence based on the region of the body being scanned. Each scanning sequence is precisely timed, and directed to a series of pulse sequences for each data sampling window. Thus an imaging procedure for one region of the body may result in one or more scanned images.

Typically, a MRI operator monitors and controls the system and selects the predetermined scanning sequence from a menu driven program. Once the patient is arranged in the stationary magnetic field, the central controller can execute the program modules to direct the MRI scanner to initiate the predetermined scanning sequences for that body part. When one pulse sequence is completed, central controller may prompt the operator to enter another pulse sequence. This process can be repeated until the predetermined scanning sequence is completed.

Once the image is generated it is available for immediate viewing. Central controller can readily transmit the scanned image to a viewing console or monitor. The available image allows immediate interpretation by one skilled in the art of reading and interpreting radiographical images. Additionally, an operator may verify that the MRI scanner properly targeted the area being studied. If an interpreter is unavailable to read the image immediately, central controller may store the image along with the patient's demographic information in a large capacity storage device like a database to be retrieved at a later time.

At the time of interpretation, central controller may execute the program modules stored in program storage to locate and retrieve the patient's images for display on a viewing console. If a pathology is detected, there is a determining of the radiographical image that best depicts the pathology from the images that were produced for that region. The selected image is therefore available for further annotation and delineation of the pathology. Central controller receives a request to annotate the selected radiographical image and executes the program software modules to highlight the selected image as desired. Once the annotation is complete, the annotated scanned image is ready for customizing to be delivered in a readable format for the requesting physician, for instance, a photographical image of the annotated radiographical image can be generated. The photographical representation may be further customized to certain sizes and photographic image quality.

Accordingly, the patient and the physician benefit from this method of providing pathological information evidenced from radiographical reports. The pathology is annotated for the doctor denoting exactly where the existing pathology is located. The annotated pictorial representation is viewable without the aid of a specialized viewer, and for doctors who are not well versed in interpreting an MRI image, the annotation readily identifies the type of pathology. The physician is now better equipped with the necessary information to provide a complete diagnosis for the patient. Both patient and the doctor will benefit from the increased quality patient care as pathologies are detected and confirmed sooner, thus either preventative or corrective treatment can be implemented as required.

In general, other aspects of the invention involve additional features and advances as set forth herein and beyond those set forth, herein. The enumerated advantages and features described herein, are presented only to assist in understanding the invention. It should be understood that they are not intended to be limitations on the invention as defined by the claims, or limitations on equivalents to the claims. For instance, some of these advantages are mutually contradictory, in that they cannot be simultaneously present in a single embodiment. Similarly, some advantages are applicable to one aspect of the invention, and inapplicable to others. Thus, the specifically referred to features and advantages should not be considered dispositive in determining equivalence.

Additional features and advantages of the invention will become apparent in the following description, from the drawings, and from the claims.

BRIEF DESCRIPTION OF THE DRAWINGS

The accompanying drawings illustrate certain embodiments of the invention.

DETAILED DESCRIPTION OF PREFFERRED EMBODIMENTS

Figure 1:
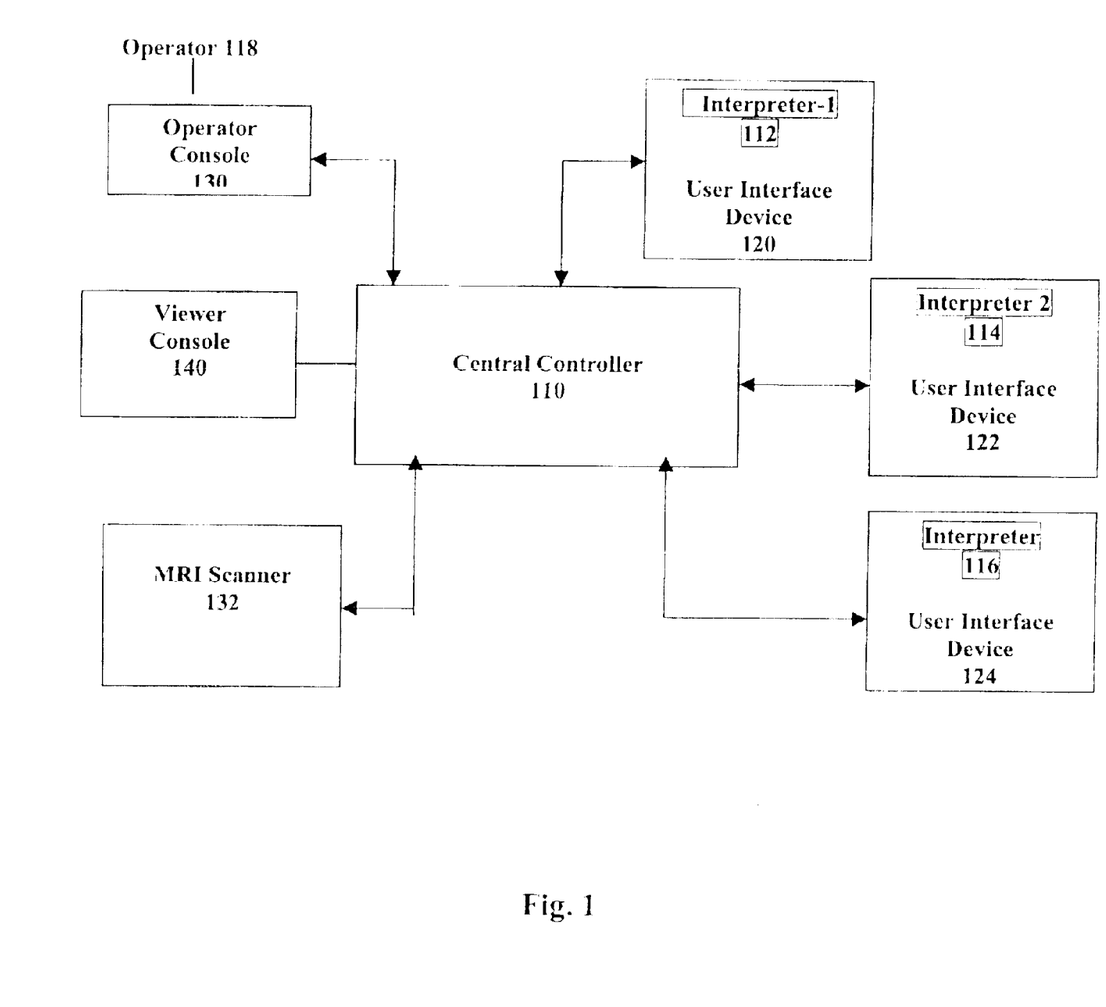
FIG. 1 illustrates an example of the functional components of a system in accordance with the present invention.

FIG. 1 illustrates an example of the functional components of a system in accordance with the present invention. As described below, the system and method allows for the provision of information concerning pathological findings evidenced by radiographical reports. The system incorporates a number of functional components. In the illustrated embodiment, the system comprises of a central controller 110 electronically coupled to a MRI scanner 132, operator console 130, and a viewer console 140. The system may also have interpreters 112, 114, 116 linked in a network wherein the interpreters 112, 114, 116 can readily access the patient's images at their convenience for reading and interpretation using interface devices 120, 122, 124.

As is well known, the MRI scanner 132 comprises, in general, of a current supply device and a measuring station, which includes magnets for the creation of high frequency magnetic pulses. The magnet of the MRI scanner 132 is preferably in an open configuration providing easy access to the patient supported on a bed or a table. In another embodiment, the MRI scanner 132 is a closed configuration. Installations of these types of MRI scanners 132 are generally well known in the art and are commercially available, such that further explanation of the details of the MRI scanner 132 is unnecessary. The MRI scanner 132 creates signals that are responsible for generating an image which is sensitive enough that the various organs and/or tissues can be differentiated.

The central controller 110 provides control, signal processing and message display modules for the system. The central controller 110 also controls the MRI scanner's 132 signal transmissions as it scans the patient. The operator console 130 is coupled to the central controller 110 and allows the operator 118 to communicate with and control the system. Depending on the region of the body that is being studied, the operator 118 will need to enter selections via the operator console 130 to direct the imaging process. Central controller 110 receives the instructions for imaging and executes the appropriate program modules to scan the patient in accordance with the region of the body being studied. The area being studied will dictate the predetermined scanning sequence, pulse sequences and the imaging angles. Typically, the operator 118 selects a particular predetermined scanning sequence from a set of options in a menu driven program. When one pulse sequence is completed, the operator 118 can request another pulse sequence which can then be initiated by the central controller 110. The system may also have a viewer console 132 to allow a viewer to view the MRI images that are being produced in real time or almost real time. In one embodiment, the operator 118 and the viewer are the same.

In the illustrated embodiment, the central controller 110 is electronically linked to interpreters 112, 114, 116 in a network. Interpreters 112, 114, 116 represent entities with the requisite skill, knowledge and experience to read and interpret a patient's MRI images. Interpreters 112, 114, 116 generally comprise of clinicians, for example, radiologists or other medical care providers. In the preferred embodiment, the interpreters 112, 114, 116 are electronically linked to the system such that they can readily access the patient's images 370 at their convenience for review and interpretation.

Depending upon the implementation, the interpreters 112, 114, 116 communicate with the central controller 110 via user interface devices 120, 122, 124 that may comprise of one or more blue-toothed device a telephone, a conventional computer, internet device, online or internet access device, noise response unit, a monitor, a keyboard and/or other components that may allow an interpreter 112 to implement the commands, and the software and hardware functions described herein. The interpreters 112, 114, 116 can therefore access the patient's MRI images 370 online and prepare their respective reports accordingly.

The operator 118, for all intents and purposes, is considered functionally the same as the operator 118 discussed in connection with FIGS. 1 and 2. An operator 118 represents a medical service provider who operates the MRI scanner 132 and monitors the scanned images for accuracy in accordance with the study description 350 prescribed by the referring physician 340. In practice, the operator 118 is the technician who ensures that the patient is optimally placed for imaging as well as verifies that the MRI scanner 132 is properly directed to the region of the body being scanned. In one embodiment, the operator 118 and the interpreter 112 are one entity, for instance a solo practioner radiologist who operates the MRI scanner 132. In another embodiment, the interpreters 112, 114, 116 and the operator 118 are two separate and distinct entities. For example, the interpreters 112, 114, 116 are generally distinguishable from the technician/operator 118 of the MRI scanner 132. It is presumed understood that neither the operator 118 nor the interpreters 112, 114, 116 are functionally part of the invention.

Figure 2:
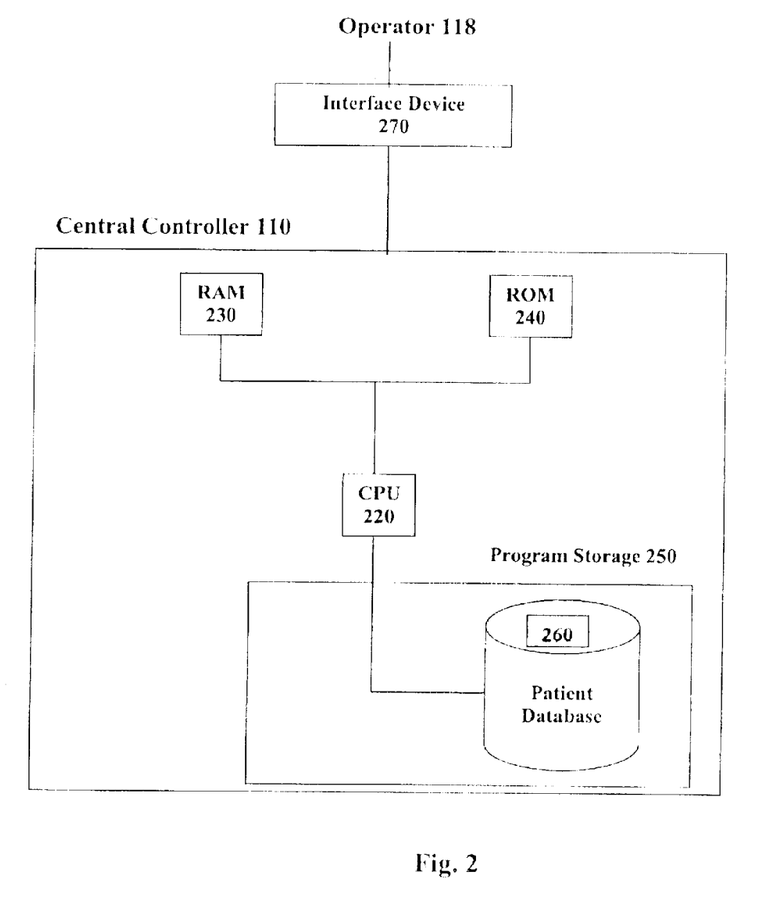
FIG. 2 illustrates an example computer suitable for use in accordance with the invention.

FIG. 2 is a simplified block diagram of the hardware elements of a central controller 110 suitable for implementation of one or more of the functional blocks of FIG. 1. As shown, the central controller 110 includes random access memory ("RAM") 230, read-only memory ("ROM") 240, program storage device 250 with one data storage device 260, and a central processing unit ("CPU") 220. CPU 220 interacts with RAM 212, ROM 214, and program storage 250 to execute program code in a conventional manner.

The CPU 220 preferably comprises of one or more conventional microprocessors such as Intel® Pentium® processor of suitable digital speed and processing power to accomplish the functions and tasks described herein. The CPU 220 is connected to RAM 220 and ROM 230 to facilitate execution of a program obtained from program storage 250 or for processing data received via communication interface device 270. The program storage 250 contains the program modules that implement the functionality of one or more of the particular functional system elements.

The communication interface 270 allows the central controller 110 to communicate, for example, with the operator 118 and/or other central controllers 110 if they are implementing functions of the database 260 that are not implemented by that central controller 110. Depending upon the particular functional element or elements it implements, the central controller 110 may be a basic computer such as an IBM personal computer, a single or multi-processor web server, a mainframe central computer or even a highly parallel computer. As described in further detail below, the central controller 110 stores the information received from the MRI scanner 132 in the patient database 260 as more fully described in FIG. 3.

An illustrative sample of the patient database 260 is shown and described in connection with FIG. 3. The specific data and fields illustrated in these figures are representative of one embodiment of the records stored in the patient database 260.

Figure 3:
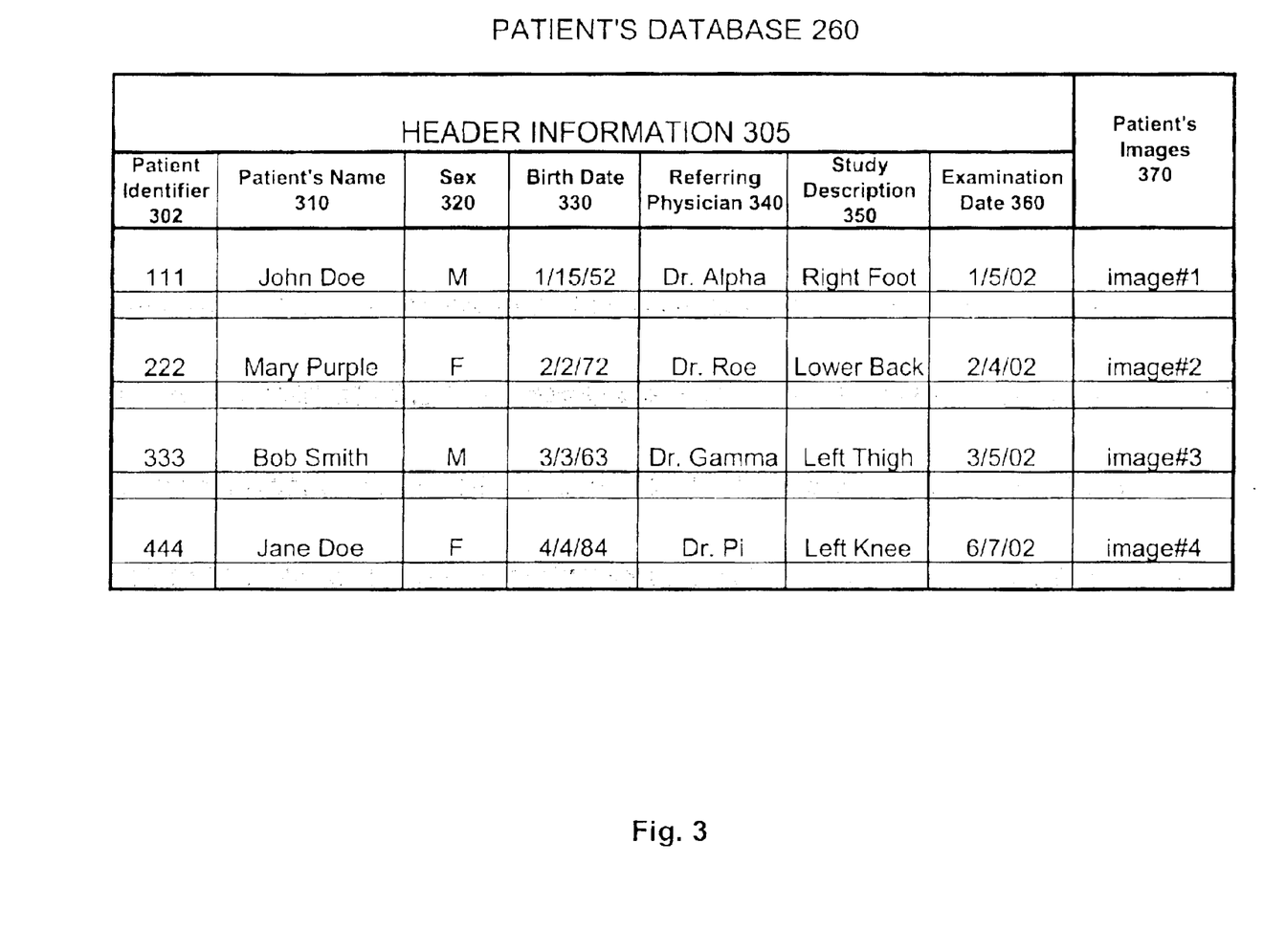
FIG. 3 is one example of a portion of a simplified database according to the present invention.

In most cases, the fields shown in FIG. 3 are self-explanatory. In one embodiment, the patient's demographic information is stored as header for the patient's images 370. It is to be understood that the data fields, as well as the number of databases 260, can be readily modified from the described embodiment, and adapted to provide variations for operating the system and method described, and/or the storage capacity of the medical service provider's system. Furthermore, each field may contain more or less information. For example, the patient identifier 302 field may comprise of separate fields containing social security number, street address, apartment number, city, state, zip code and telephone number, as well as an email address.

FIG. 3 illustrates one representative example of the contents of the patient database 260 stored in the central controller 110. As shown, the patient database 260 includes at least four patient entries. Each entry is representative of a patient's MRI image study. Typically, radiographical images are stored in DICOM format with the demographic information (for example, name, sex, birth date, referring physician, study description, examination date) stored in the header 305. For illustrative purposes, each field of the header 305 is described as a separate data field. Patient database 260 contains fields relating to patient identifier 302, patient's name 310, sex 320, birth date 330, referring physician 340, study description 350, an examination date 360, and patient's images 370. As described in more detail below, the central controller 110 uses the patient identifier 302 to identify and access the patient's images 370. The central controller 110 also uses the patient identifier 302 to track the services rendered for later reporting and billing purposes. An interpreter 112 may use the patient's sex and birth date 330 in their diagnostic evaluations of the images.

Figure 4A:
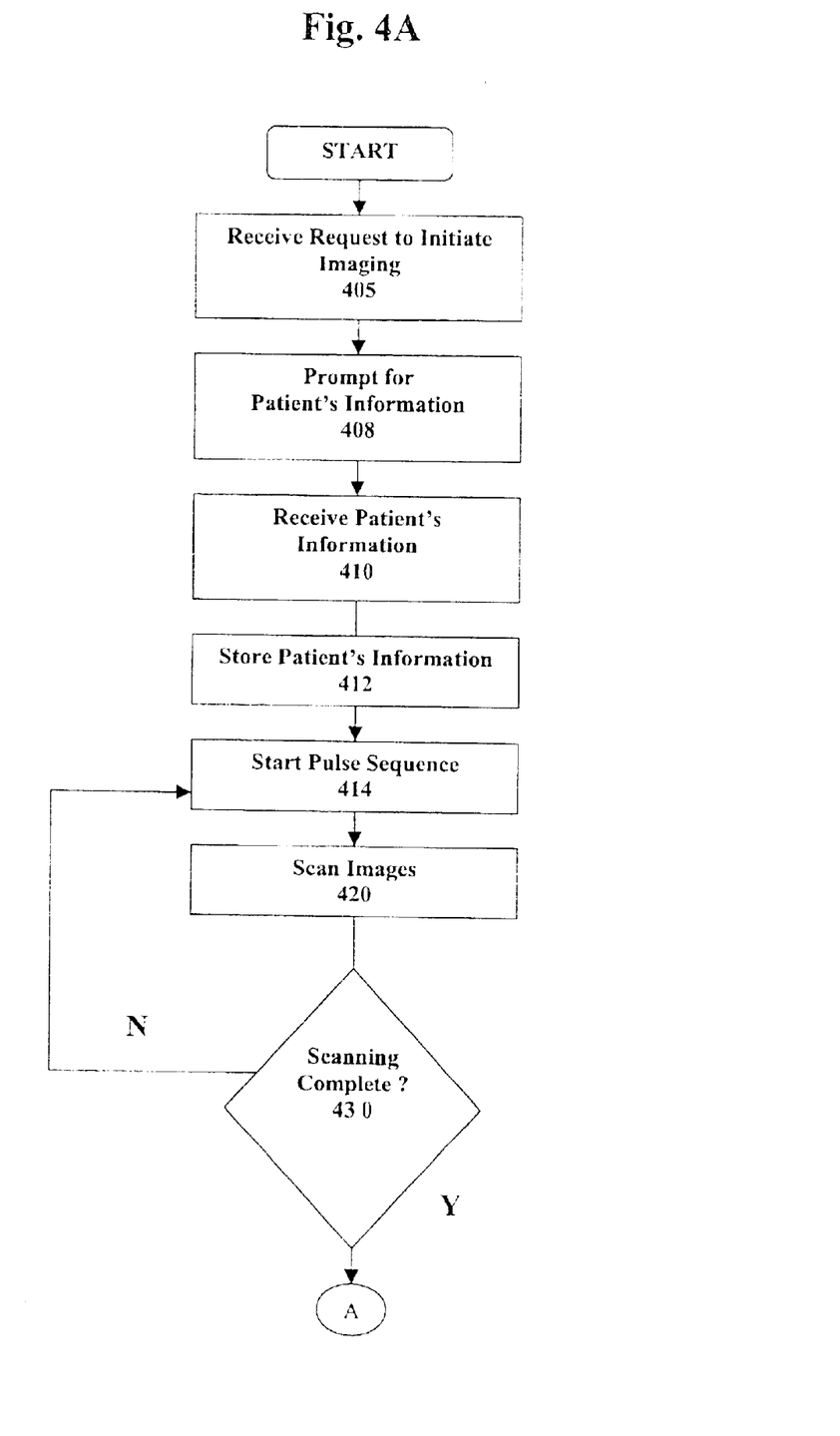
FIGS. 4A–4C are example flowcharts for a process operating in accordance with the present invention.
Figure 4B:
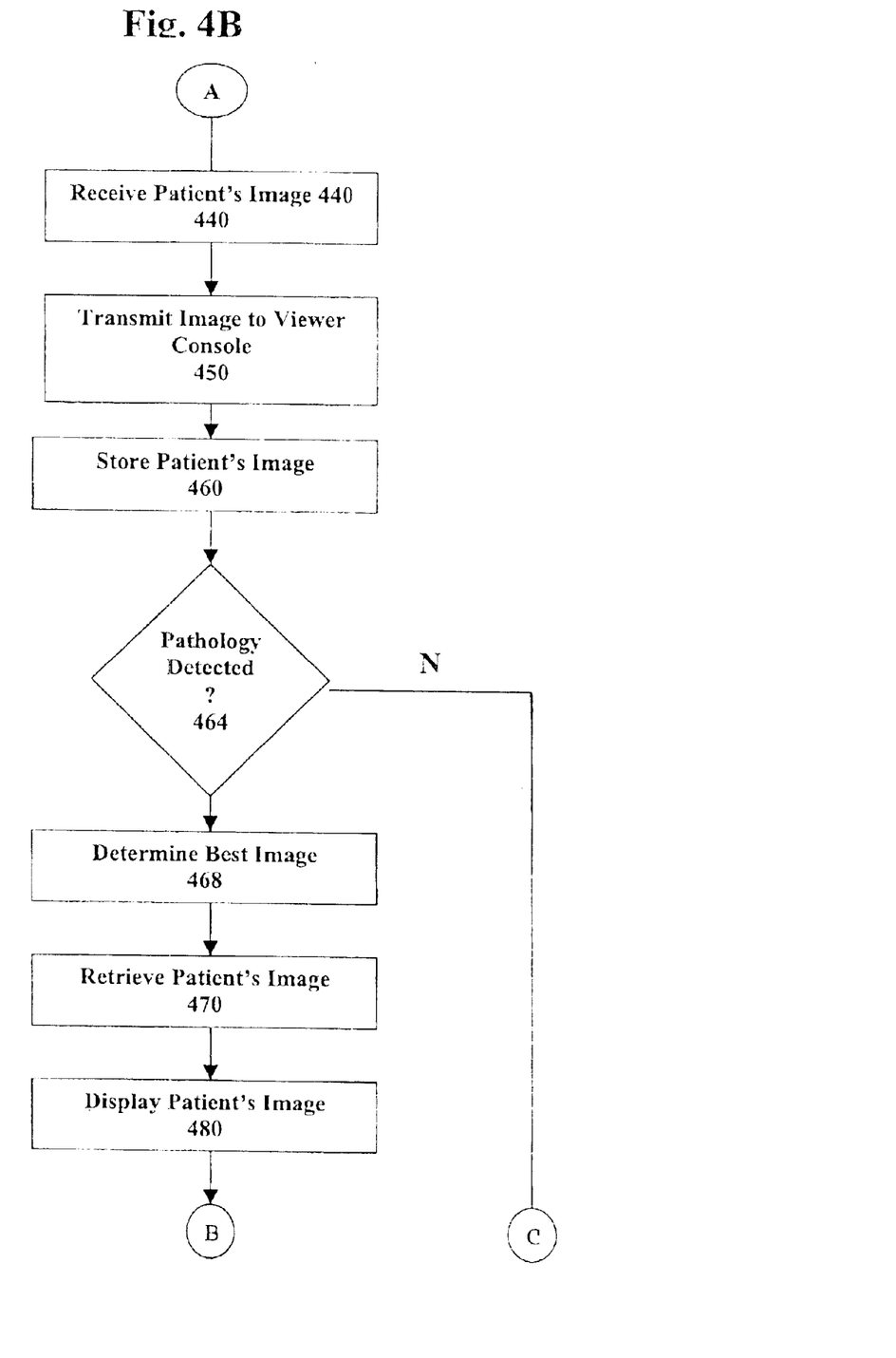
Figure 4C:
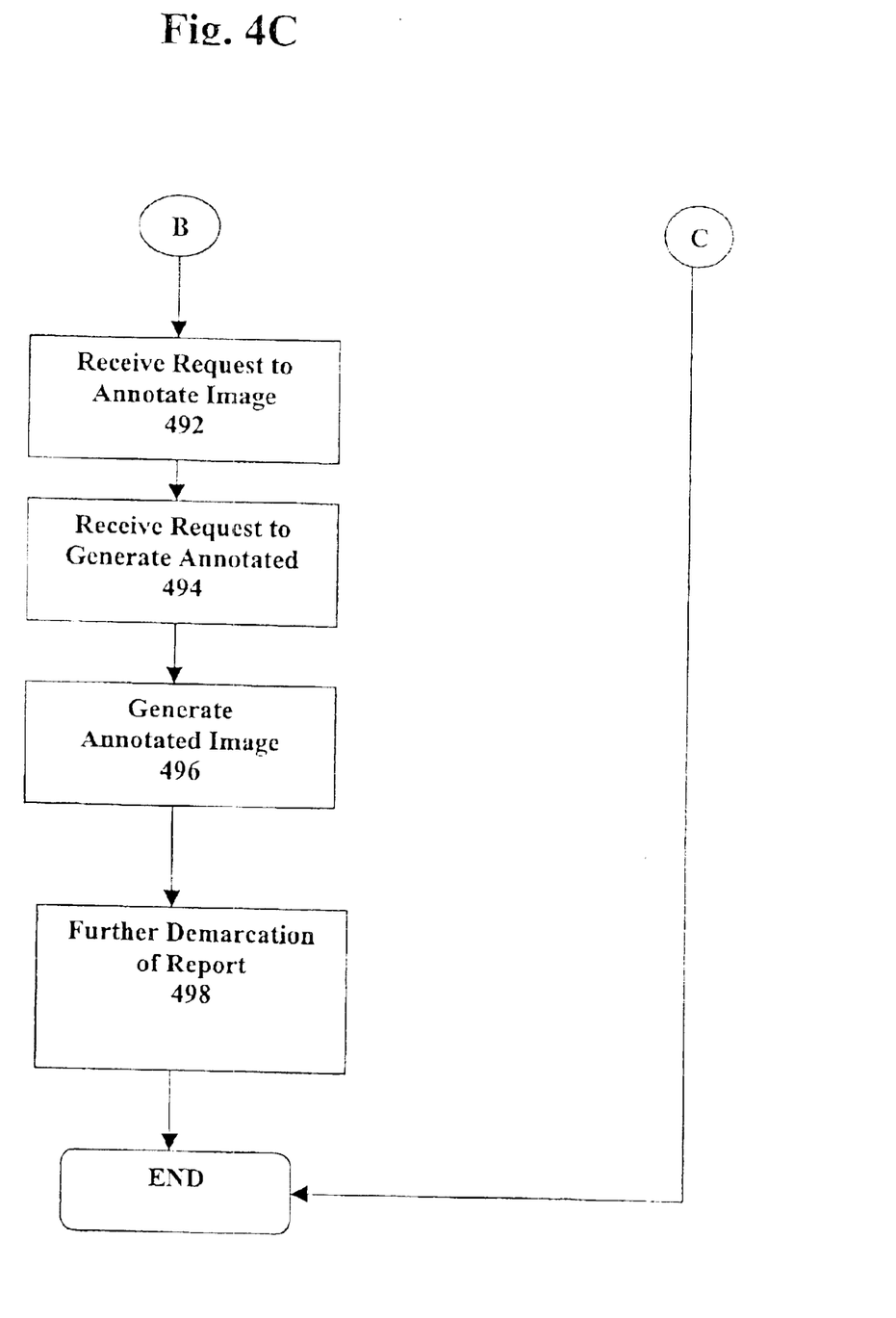

FIGS. 4A–4C are example flowcharts of a process operating in accordance with the present invention. The process of using data from the patient database 260 to fulfill the system and method illustrated in FIGS. 1 and 2 is represented in FIGS. 4A–4C.

The reporting process is initiated (step 405) when the central controller 110 receives a request to initiate radiographical imaging of a patient. Central controller 110 using the program modules stored in the CPU 220 may prompt the operator 118 to enter the patient's demographic information (step 408). In one embodiment the patient may supply a referral letter from the referring physician 340 detailing the patient's vital information, for example, the patient's name 310, sex 320, birth date 330, referring physician's name 340, and the requested study description 350. In another embodiment, the patient supplies their vital information directly to the medical service provider along with a limited written prescription for the study description 350. In step 410, central controller 110 executes program modules stored in the CPU 220 to receive patient's name 310, sex 320, birth date 330, referring physician 340 and study description 350. Central controller 110 may temporarily store patient's information in a data storage device like the patient database 260 (step 412).

After the patient is identified to the system, central controller 110 may prompt the operator 118 to start pulse sequences (step 414). The operator 118 can select options generally from a menu driven program to commence the imaging study of the patient based on the study description 450 prescribed by the referring physician 440. Imaging of a region requires that the patient is properly placed on a stationary magnetic filed, which in the preferred embodiment is an open MRI scanner 132 with a table or a bed for the patient. The operator 118 may select a particular predetermined scanning sequence or sequences based on the portion of the body being scanned and the instructions of the referring physician 340.

Central controller 110 in step 420 executes the commands and program modules to initiate a sequence of pulses in order to capture an image of the requested study. A single study description 350 may require more than one image captured from different angles. Once a pulse sequence is completed central controller 110 verifies in step 430 if the scanning sequence is completed for that region. If the scanning sequence is incomplete, central controller 110 may prompt the operator 118 to begin another pulse sequence, which can then be initiated by the central controller 110 and the imaging process is repeated from steps 414–430. However, if the scanning sequence is complete, then central controller 110 receives the patient's image 370 from the MRI scanner 132 (step 440), and can transmit the image to a viewer console 140 (step 450) to allow the viewing of the patient's images 370 in real time or almost real time for accuracy. The patient's images 340 are also available for immediate interpretation by an interpreter 112. However, the interpretation may be done at a later time.

In the illustrated embodiment, central controller 110 stores the completed collected patient's images 370 in a large capacity data storage device like the patient database 260 (step 460). Each patient's image 370 may be stored in DICOM format with the patient's information stored in the header 305. The stored patient's images 370 are therefore readily identifiable and available for review and interpretation at a more opportune time.

In one embodiment, the interpreter 112 consists of a radiologist or a member of a practicing group of radiologists who are linked to the central controller 110 via a network and can access the stored patient's images 370 online. In another embodiment, the interpreters 112, 114, 116 may comprise of one or more individual radiologists who are not electronically linked to the central controller 110 and must review a hard copy of the patient's images 370. In step 464, the patient's images are reviewed to determine if there is a pathology.

Generally, an interpreter 112 prepares a written report describing the findings evidenced by the patient's images 370 and notes for the referring physician 340 if there is a positive finding of a pathology. If no pathology is detected the written report as well as the patient's images 370 are submitted to the referring physician 340 who may maintain the patient's images 370 as future baseline references. If a pathology is detected, one skilled in the art of interpreting radiographical images, for instance, an interpreter 112, or an operator 118 evaluates the individual patient's images 370 and identifies the patient's image 370 that best depicts the detected pathology (step 468). The patient's image 370 is then selected for annotation.

In one embodiment, the patient's images 370 are already stored in a storage device like patient database 260 and the patient's images need to be retrieved in order for it to be annotated. In step 470, central controller 110 receives a request to retrieve the patient's image 370 that was previously selected for further annotation. Central controller 110 executes the necessary program modules stored in program storage 250 to locate and retrieve patient's image 370 and displays the retrieved patient's image (step 480) on a screen monitor, for example, a viewer console 140.

In general, one skilled in the art of the invention, for example, an interpreter 112 or an operator 118, may enter a request to annotate the selected patient image 370 with drawings, figures and written descriptions. In step 492, central controller 110 receives the request to annotate the retrieved patient's image 370 and executes the program modules of the software necessary to annotate the patient's image 370. The interpreter 112 or the operator 118 may select various combinations of lines, arrows, drawings, colors or other demarcations as needed to appropriately highlight the pathology. Once the annotation is complete the annotated patient's image 370 is ready for printing in its finalized form. The operator 118 or the interpreter 112 may enter a request for the annotated image to be generated and may select particular parameters, for example, image size for the printed copy. Central controller 110 receives the request in step 494 to generate the modified annotated patient image 370 by preparing a photograph of the annotated radiographical image (step 496) for submission to the referring physician 340. In one embodiment the completed report is provided to the referring physician 340 as a written report. In another embodiment the information is provided as an electronic copy. The system and method terminates (step 498) after executes program modules of the software to further highlight the MRI imaging study for delivery to the referring physician 340 with demarcations on the MRI imaging study report alerting the referring physician 340 of a detected pathology as shown in FIG. 5.

Figure 5:
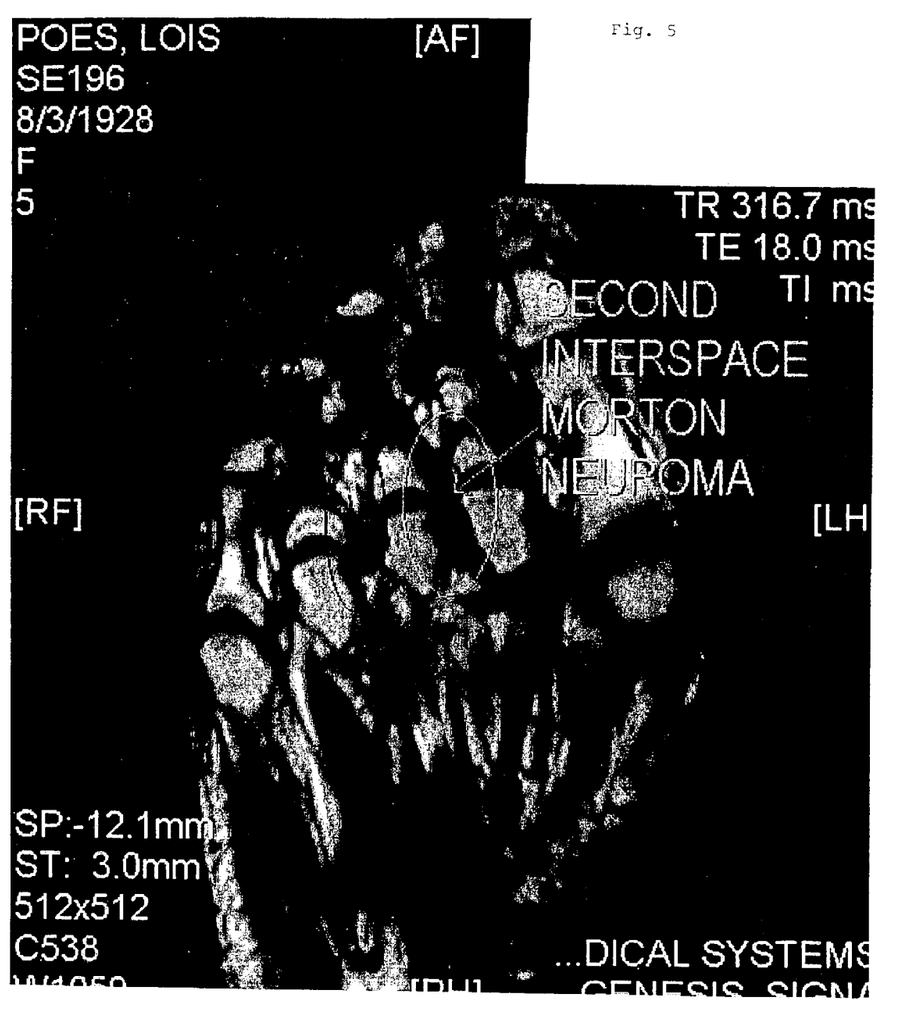
FIG. 5 is an example chart in detail of the annotated patent's image in a practical performance of an embodiment of the invention.

As illustrated, FIG. 5 displays an annotated photographic image displaying the patient's demographic information, i.e., patient's name 310, sex 320, birth date 330, referring physician 340, study description 350, and examination date 360. According to the study description 350 the "RT [right] FOOT" was imaged. In this embodiment, two pathologies consisting of morton nueromas were detected from the radiographical images of the patient's right foot. As illustrated, the nueromas were highlighted, circled and clearly marked with arrows providing a ready description and pictorial image of the detected pathology.

Figure 6:
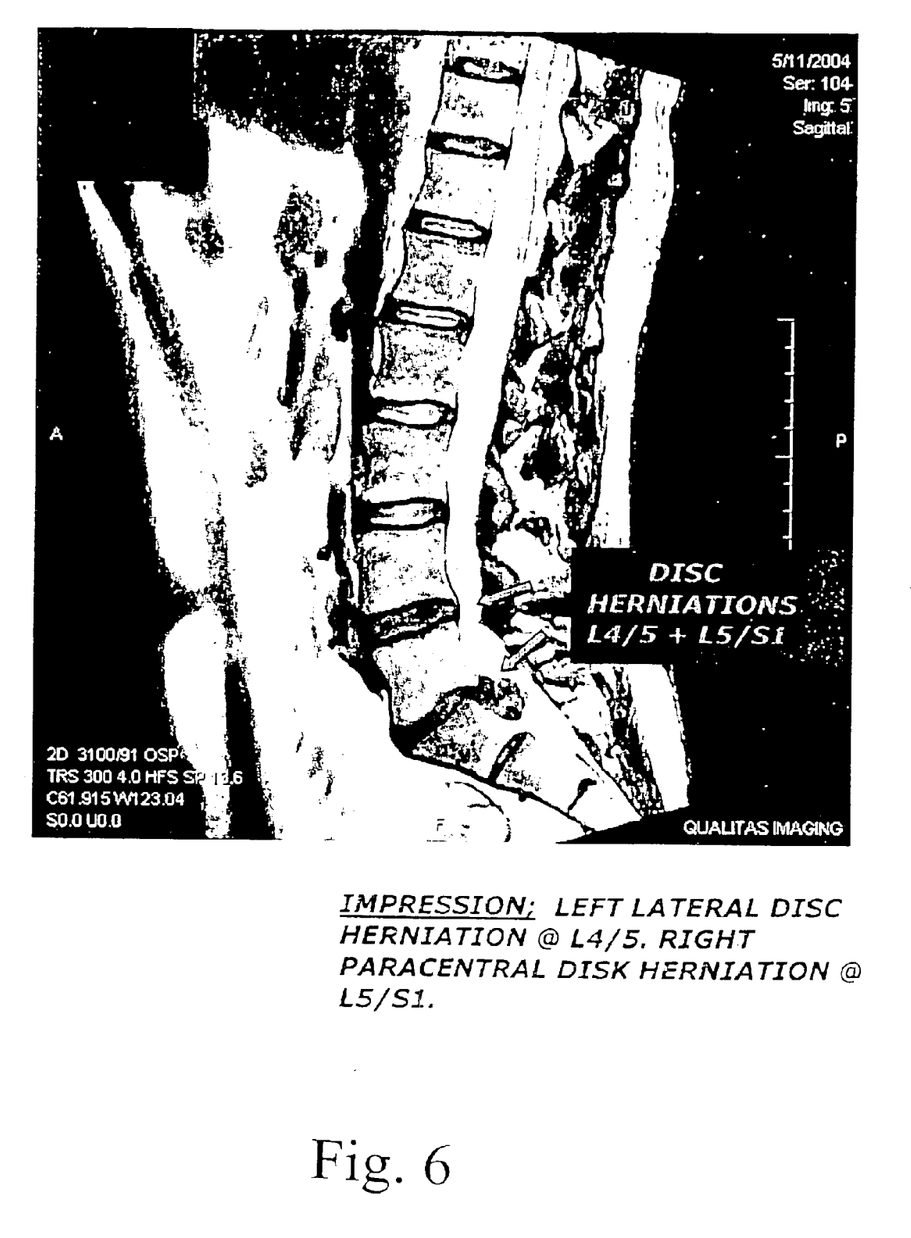
FIG. 6 is an example chart in detail of the demarcated report in a practical performance of an embodiment of the invention.

FIG. 6 is an example chart in detail of the demarcated report in a practical performance of an embodiment of the invention. As illustrated, the pictorial image is highlighted with further demarcation alerting a reader of a positive finding of the detected pathology in the annotated radiographical image. A demarcation may comprise of an identifying mark, red flags, or statement informing the reader of a pathology.

Having described the invention in a simplified manner for purposes of understanding, it will be recognized that numerous more complex and/or commercially suitable arrangements are possible.

It should be apparent that although various processes and implementations have been discussed, in many cases, some of those processes or their component parts can happen in different orders or concurrent with other steps. Similarly, various implementation differences can readily be employed, such as a plurality of databases. Thus, while a number of embodiments have been shown and described, it should be understood that the above description is only representative of illustrative embodiments. For convenience, the above description has focused on a representative sample of all possible embodiments, a sample that teaches the principles of the invention, further embodiments may also result from a different combination of described portions of different embodiments. The description has not attempted to exhaustively enumerate all possible variations. That alternate embodiments may not have been presented for a specific portion of the invention, may result from a different combination of described portions of different embodiments, or that further undesired alternate embodiments may be available for a portion, is not to be considered a disclaimer of those alternate embodiments. It will be appreciated that many of those undescribed embodiments are literally within the scope of the invention and others are equivalent.

What is claimed is:

1. A method for communicating a radiologist's or skilled interpreter's findings directly on diagnostic images comprising:

viewing more than one diagnostic image of a region of an object that is generated by a diagnostic medical imaging machine and verifying via a radiologist's or skilled interpreter's findings if there is a detectable pathology depicted in any of the diagnostic images;

reviewing each diagnostic image having a detectable pathology;

selecting as a result of said reviewing step the diagnostic image that best depicts the detected pathology;

receiving an interpreter's request to annotate the diagnostic image that was selected;

annotating the diagnostic image that was selected by delineating the detected pathology via inserting indicia on said image, based upon the radiologist's or skilled interpreter's findings whereby the indicia includes reference designations for immediately locating the pathology and wording to identify the type of pathology; and generating an annotated diagnostic image highlighting the detected pathology via said indicia thereon.

2. The method according to claim 1, wherein the region of an object further comprises a region of a human body.

3. The method according to claim 1, wherein the diagnostic medical imaging machine further comprises a Magnetic Resonance Imaging scanner.

4. The method according to claim 1, wherein the detected pathology further comprises an abnormality.

5. The method according to claim 1, wherein the reviewing step further comprises comparing each diagnostic image with a written description of the detected pathology.

6. The method according to claim 1, wherein the generating step further comprises preparing a display of the annotated diagnostic image in the form of an electronic copy, a photograph or a printout.

7. The method according to claim 1, wherein the generating step further comprises preparing a display of the annotated diagnostic image in the form of an electronic copy.

8. A programmed computer for communicating a radiologist's or skilled interpreter's findings directly on diagnostic images, comprising:

a memory and a processor, the memory having at least one program module which when executed by the processor performs the method of claim 1.

9. A method for communicating a radiologist's or skilled interpreter's findings directly on diagnostic images comprising:

receiving a first request to initiate diagnostic imaging of a region of an object with a diagnostic medical imaging machine;

scanning the object using the diagnostic medical imaging machine in accordance with a predetermined scanning sequence for the region of the object being scanned;

generating at least one diagnostic image of the object being scanned to permit a radiologist or skilled interpreter to determine if there is a detected pathology;

receiving a second request to annotate a diagnostic image that was selected based upon said radiologist or skilled interpreter determining a detected pathology, whereby indicia is inserted on said image, the indicia including both reference designations for immediately locating the pathology, and wording to identify the type of pathology;

generating an annotated diagnostic image highlighting the detected pathology; and preparing a display in the form of an electronic copy, a photograph or a printout of the annotated diagnostic image.

10. The method according to claim 9, wherein the diagnostic medical imaging machine further comprises a Magnetic Resonance Imaging scanner.

11. The method according to claim 9, wherein the object further comprises a region of a human body.

12. The method according to claim 9, wherein the detected pathology further comprises an abnormality.

13. The method according to claim 9, wherein the predetermined scanning sequence further comprises more than one image of the region of the object.

14. The method according to claim 9, further comprising verifying that a scanning sequence is complete based upon the predetermined scanning sequence for the region of the object being scanned.

15. The method according to claim 9, further comprising receiving patient information.

16. The method according to claim 15, further comprising storing patient information in a database.

17. The method according to claim 9, further comprising storing diagnostic images in a database.

18. The method according to claim 17, further comprising receiving a request to retrieve diagnostic images from a database.

19. The method according to claim 18, further comprising retrieving the diagnostic image and displaying a retrieved image.

20. A programmed computer for communicating a radiologist's findings directly on diagnostic images, comprising:

a memory and a processor, the memory having at least one program module which when executed by the processor performs the method of claim 9.

21. A system for communicating a radiologist's or skilled interpreter's findings directly on diagnostic images, comprising:

a central controller configured for receiving a request to annotate a diagnostic image of a region of an object in which a pathology was detected;

said central controller being configured for annotating the diagnostic image by delineating the detected pathology with at least one marking based upon a radiologist's or skilled interpreter's findings, whereby the at least one marking includes both reference designations for immediately locating the pathology, and wording to identify the type of pathology;

said central controller being configured for generating an annotated diagnostic image highlighting the detected pathology, and preparing a display in the form of an electronic copy, photograph or printout of the annotated diagnostic image.

22. The system according to claim 21, wherein the central controller is further configured for receiving a patients demographic information.

23. The system according to claim 22, wherein the central controller is further configured for storing the patient's demographic information in a database.

24. The system according to claim 21, wherein the central controller is further configured for scanning a region of an object based on a predetermined scanning sequence for that region.

25. The system according to claim 21, wherein the central controller is further configured for verifying that the predetermined scanning sequence for that region is complete.

26. A system for communicating a radiologist's or skilled interpreter's findings directly on diagnostic images, comprising:

a central controller configured to receive transmissions of requests for performing diagnostic imaging of a region of an object by a diagnostic medical imaging machine;

said central controller being further configured to receive transmissions of requests from a radiologist or skill interpreter for annotating diagnostic images of the region of an object for which a pathology is detected, and annotating the diagnostic image of a region of an object by delineating the detected pathology with at least one marking based upon a radiologist's or skilled interpreter's findings;

said central controller being further configured to generate an annotated diagnostic image highlighting the detected pathology, and prepare a display in the form of an electronic copy, a photograph or a printout of the annotated diagnostic image; and a database for storing patient information containing data, at least some of the data collectively representing a diagnostic imaging study.

27. The system of claim 26, further comprising:

means for receiving transmissions of requests to perform diagnostic imaging of the object by the diagnostic medical imaging machine.

28. The system of claim 26, further comprising:

means for receiving transmissions of requests to annotate diagnostic images of the object for which a pathology is detected.

29. The system of claim 26, further comprising:

means for storing patient information in the database containing data, at least some of the data collectively representing the diagnostic imaging study.

30. The system of claim 29, further comprising:

means for delineating the detected pathology with at least one marking, and generating the annotated diagnostic image highlighting the detected pathology by preparing a display in the form of an electronic copy, a photograph or a printout of the annotated diagnostic image.

31. Computer executable software code stored on a computer readable medium, the code for providing communication of a radiologist's findings directly on diagnostic images comprising:

code for receiving a request to annotate a diagnostic image of a region of an object in which a pathology is detected by a radiologist or skilled interpreter;

code for annotating the diagnostic image by delineating the detected pathology with at least one marking, based upon the radiologist's or skilled interpreter's findings, whereby the at least one marking includes reference designations for immediately locating the pathology, and wording to identify the type of pathology; and code for generating an annotated diagnostic image highlighting the detected pathology and preparing a photograph of the annotated diagnostic image.

32. A computer readable medium having computer executable software code stored thereon, the code for providing communication of a radiologist's findings directly on diagnostic images, comprising:

code to receive a request to annotate a diagnostic image of a region of an object in which a pathology is detected by a radiologist or skilled interpreter;

code for annotating the diagnostic image by delineating the detected pathology with at least one marking, based upon the radiologist's or skilled interpreter's findings, whereby the at least one marking includes reference designations for immediately locating the pathology and wording to identify the type of pathology;

code for storing patient information in a database;

code to compile and monitor databases; and code for generating an annotated diagnostic image highlighting the detected pathology and preparing a display in the form of an electronic copy, a photograph or a printout of the annotated diagnostic image.

33. A computer readable medium having modules for providing communication of a radiologist's findings directly on diagnostic images stored thereon, comprising:

a module that, when executed, processes a received transmission to annotate a diagnostic image of a region of an object in which a pathology is detected as determined by a radiologist or skilled interpreter;

a module that, when executed, annotates the diagnostic image by delineating the detected pathology with at least one marking, based upon the radiologist's or skilled interpreter's findings, whereby the at least one marking includes reference designations for immediately locating the pathology and wording to identify the type of pathology; and a module that, when executed both generates an annotated diagnostic image highlighting the detected pathology and prepares a display in the form of an electronic copy, a photograph or a printout of the annotated diagnostic image.

34. A method for communicating a radiologist's or skilled interpreter's findings directly on diagnostic images comprising:

establishing a communication network comprising a plurality of communication terminals each being selectively operable for communication with a diagnostic medical imaging machine;

viewing, via at least one of said plurality of communication terminals, more than one diagnostic image of a region of an object that is generated by the diagnostic medical imaging machine, and verifying from a radiologist's or skilled interpreter's findings if there is a detectable pathology depicted in any of the diagnostic images;

reviewing, via one of said plurality of communication terminals, each diagnostic image having a detectable pathology;

selecting, via one of said plurality of communication terminals, as a result of said reviewing step, the diagnostic image that best depicts the detected pathology;

receiving a radiologist's or skilled interpreter's request, from one of said plurality of communication terminals, to annotate the diagnostic image that was selected;

annotating the selected diagnostic image, via one of said plurality of communication terminals, by delineating the detected pathology via inserting indicia on said image, based upon the radiologist's or skilled interpreter's findings, whereby the indicia includes both reference designations for immediately locating the pathology, and wording to identify the type of pathology;

generating, via one of said plurality of communication terminals, an annotated diagnostic image highlighting the detected pathology; and preparing a display in the form of an electronic copy, a photograph or a printout of the annotated diagnostic image including said indicia.

* * * * *